United States Patent
Pando et al.

(10) Patent No.: US 8,840,892 B2
(45) Date of Patent: Sep. 23, 2014

(54) METHOD OF ADMINISTERING ANTIBIOTIC THERAPY FOR TREATING INTRACELLULAR INFECTIOUS DISEASES

(75) Inventors: Rogelio Hernandez Pando, San Miguel Topilejo (MX); Fernando Lopez Casillas, San Miguel Topilejo (MX)

(73) Assignee: Universidad Nacional Autónoma de México, Delegación Coyoacán (MX)

( * ) Notice: Subject to any disclaimer, the term of this patent is extended or adjusted under 35 U.S.C. 154(b) by 1695 days.

(21) Appl. No.: 10/556,376

(22) PCT Filed: May 12, 2004

(86) PCT No.: PCT/MX2004/000031
§ 371 (c)(1),
(2), (4) Date: Nov. 10, 2005

(87) PCT Pub. No.: WO2004/100864
PCT Pub. Date: Nov. 25, 2004

(65) Prior Publication Data
US 2006/0251657 A1    Nov. 9, 2006

(30) Foreign Application Priority Data
May 13, 2003   (MX) .................... PA/a/2003/004172

(51) Int. Cl.
A61K 39/395   (2006.01)
A61K 31/415   (2006.01)
A61K 31/195   (2006.01)
A61K 31/715   (2006.01)

(52) U.S. Cl.
CPC .................................. *A61K 31/715* (2013.01)
USPC ................... 424/145.1; 514/406; 514/562

(58) Field of Classification Search
None
See application file for complete search history.

(56) References Cited

U.S. PATENT DOCUMENTS

2001/0047024 A1*   11/2001   Seibert et al. ............... 514/406

FOREIGN PATENT DOCUMENTS

WO    WO 9310215   *   5/1993

OTHER PUBLICATIONS

Moreno et al. (Immunology 2002, vol. 106 pp. 257-266).*
Attisano, L., et al., "TGF-β receptors and actions," *Biochimica et Biophysica Acta 1222*:71-80, Elsevier Ltd. (1994).
Barral-Netto, M., et al.,"Transforming Growth Factor-β in Leishmanial Infection: A Parasite Escape Mechanism," *Science 257*: 545-548, American Assn. for the Advancement of Science (1992).
Barral-Netto, M., et al.,"Cytotoxicity in human mucosal and cutaneous leishmaniasis," *Parasite Immunology 17*:21-28, Blackwell Scientific Publications (1995).
Betz, M. and Fox, B.S., "Prostaglandin $E_2$ Inhibits Production of Th1 Lymphokines But Not of Th2 Lymphokines," *J. Immunol. 146*:108-113, American Association of Immunologists (1991).
Brown, C.B., et al., "Requirement of Type III TGF-β Receptor for Endocardial Cell Transformation in the Heart," *Science 283*:2080-2082, American Assn. for the Advancement of Science (1999).
Czarniecki, C.W., et al., "Transforming Growth Factor $β_1$ Modulates the Expression of Class II Histocompatibility Antigens on Human Cells," *J. Immunol. 140*:4217-4223, American Association of Immunologists (1988).
Esparza-López, J., et al., "Ligand Binding and Functional Properties of Betaglycan, a Co-receptor of the Transforming Growth Factor-β superfamily. Specialized Binding Regions for Transforming Growth Factor-β and Inhibin A," *J. Biol. Chem. 276*:14588-14596, American Society for Biochemistry and Molecular Biology (2001).
Gazzinelli, R.T., et al., "The microbicidal activity of interferon-γ-treated macrophages against *Trypanosoma cruzi* involves an L-arginine-dependent, nitrogen oxide-mediated mechanism inhibitable by interleukin-10 and transforming growth factor-β," *Eur. J. Immunol. 22*:2501-2506, VCH Verlagsgesellschaft (1992).
Goto, T., et al., "Cyclic AMP as a Mediator of Prostaglandin E-Induced Suppression of Human Natural Killer Cell Activity," *J. Immunol. 130*:1350-1355, (1983).
Hernández-Pando, R., et al., "Correlation between the kinetics of Th1/Th2 cells and pathology in a murine model of experimental pulmonary tuberculosis," *Immunology 89*:26-33, Blackwell Scientific Publications (1996).
Hernández-Pando, R., et al., "Analysis of the local kinetics and localization of interleukin-1α, tumour necrosis factor-α and transforming growth factor-β during, the course of experimental pulmonary tuberculosis," *Immunology 90*:607-617, Blackwell Scientific Publications (1997).
Hirsch, C.S., et al., "In vitro restoration of T cell responses in tuberculosis and augmentation of monocyte effector function against *Mycobacterium tuberculosis* by natural inhibitors of transforming growth factor β," *Proc. Natl. Acad. Sci. USA 94*:3926-3931, National Academy of Sciences (1997).

(Continued)

*Primary Examiner* — Robert A Zeman
(74) *Attorney, Agent, or Firm* — Sterne, Kessler, Goldstein & Fox P.L.L.C.

(57) ABSTRACT

The present invention describes the use of immunomodulators to support the usual treatment against infectious diseases caused by facultative intracellular organisms. Starting from an analysis of the immune response installed in this type of infection, particularly the infection caused by Tuberculosis, a treatment kit is used that associates a soluble betaglycan type immunomodulator, associated with an anti-inflammatory agent of the prostaglandin E blocking type, which, when used together, modulate the immune response, thus permitting a shortening in treatment time with the respective antibiotics.

9 Claims, No Drawings

(56) References Cited

OTHER PUBLICATIONS

Kehrl, J.H., et al., "Production of Transforming Growth Factor β by Human T Lymphocytes and Its Potential Role in the Regulation of T Cell Growth," *J. Exp. Med. 163*:1037-1050, Rockefeller University Press (1986).

King, C.L., et al., "Cytokine Control of Parasite-specific Anergy in Human Lymphatic Filariasis. Preferential Induction of a Regulatory T Helper Type 2 Lymphocyte Subset," *J. Clin. Invest.92*:1667-1673, American Society for Clinical Investigation (1993).

Kochi, A., "The global tuberculosis situation and the new control strategy of the World Health Organization," *Tubercle 72*:1-6, E and S Livingstone (1991).

Kuroda, E., et al.,"Sensitivity Difference to the Suppressive Effect of Prostaglandin $E_2$ Among Mouse Strains: A Possible Mechanism to Polarize Th2 Type Response in BALB/c Mice," *J. Immunol. 164*:2386-2395, American Association of Immunologists (2000).

Letterio, J.J. and Roberts, A.B., "Regulation of Immune Response by TGF-β," *Annu. Rev. Immunol. 16*:137-161, Annual Reviews (1998).

Lømo , J., et al., "TGF-β1 and Cyclic AMP Promote Apoptosis in Resting Human B Lymphocytes," *J. Immunol. 154*: 1634-1643, American Association of Immunologists (1995).

López-Casillas, F., et al., "Betaglycan Can Act as Dual Modulator of TGF-β Access to Signaling Receptors: Mapping of Ligand Binding and GAG Attachment Sites," *J. Cell Biol. 124*:557-568, (1994).

Lotz, M. and Seth, P., "TGF-β and HIV Infection," *Ann. N. Y. Acad. Sci. 685*:501-511, New York Academy of Sciences (1993).

Maeda, H., et al., "TGF-β Enhances Macrophage Ability to Produce IL-10 in Normal and Tumor-Bearing Mice," *J. Immunol. 155*:4926-4932, American Association of Immunologists (1995).

Maltman, J., et al., "Specificity and Reciprocity in the Interactions Between TGF-β, and Macrophage Inflammatory Protein 1-α," *J. Immunol. 156*:1566-1571, American Association of Immunologists (1996).

Massagué, J., "The Transforming Growth Factor-β Family," *Annu. Rev. Cell Biol. 6*:597-641, Annual Reviews (1990).

Massagué,, J., TGF-β Signal Transduction, *Annu. Rev. Biochem. 67*:753-791, Annual Reviews (1998).

Massagué, J. and Chen, Y.-G., "Controlling TGF-β signaling," *Genes and Development 14*:627-644, Cold Spring Harbor Laboratory Press (2000).

Massagué, J., et al., "TGFβ Signaling in Growth Control, Cancer, and Heritable Disorders," *Cell 103*:295-309, Cell Press (2000).

Phipps, R.P., et al., "A new view of prostaglandin E regulation of the immune response," *Immunology Today 12*:349-52, Elsevier Science Ltd. (1991).

Pinson, D.M., et al., "Regulation by Transforming Growth Factor-β1 of Expression and Function of the Receptor for INF-γ on Mouse Macrophages," *J. Immunol. 149*:2028-2034, American Association of Immunologists (1992).

Ranges, G.E., et al., "Inhibition of Cytotoxic T Cell Development by Transforming Growth Factor β and Reversal by Recombinant Tumor Necrosis Factor α," *J. Exp. Med. 166*:991-998, Rockefeller University Press (1987).

Rook, G.A.W., "The Pathogenesis of Tuberculosis," *Annual. Rev. Microbiol. 50*:259-284, Annual Reviews (1996).

Schmitt, E., et al., "T helper type 1 development of naive CD4+ T cells requires the coordinate action of interleukin-12 and interferon-γ and is inhibited by transforming growth factor-β," *Eur. J. Immunol. 24*:793-798, VCH Verlagsgesellschaft (1994).

Seah, G.T., et al., "Type 2 Cytokine Gene Activation and Its Relationship to Extent of Disease in Patients with Tuberculosis," *J. Infect. Dis. 181*:385-389, University of Chicago Press (2000).

Serhan, C.N., et al., "Lipid mediator networks in cell signaling: update and impact of cytokines," *FASEB J. 10*:1147-1158, The Federation of American Societies of Experimental Biology (1996).

Shull, M.M., et al., "Targeted disruption of the mouse transforming growth factor-β1 gene results in multifocal inflammatory disease," *Nature 359*:693-699, Nature Publishing Group (1992).

Snyder, D.S., et al., "Prostaglandins modulate macrophage Ia expression," *Nature 299*:163-165, Nature Publishing Group (1982).

Strober, W., et al., Reciprocal IFN-γ and TGF-β responses regulate the occurrence of mucosal inflammation, *Immunol. Today 18*: 61-64, Elsevier Science Ltd. (1997).

Sudre, P., et al., "Tuberculosis: a global overview of the situation today," *Bulletin of the World Health Organization 70*:149-159, World Health Organization (1992).

Toossi, Z. and Ellner, J.J., "The Role of TGFβ in the Pathogenesis of Human Tuberculosis," *Clinical Immunology and Immunopathology 87*:107-114, Academic Press (1998).

Turner, M., et al., "Induction of the interleukin 1 receptor antagonist protein by transforming growth factor-β," *Eur. J. Immunol. 21*:1635-1639, VCH Verlagsgesellschaft (1991).

Vilchis-Landeros, M.M., et al., "Recombinant soluble betaglycan is a potent and isoform-selective transforming growth factor-β neutralizing agent," *Biochem. J. 355*:215-222, Portland Press (2001).

Vodovotz, Y. and Bogdan, C., "Control of Nitric Oxide Synthase Expression by Transforming Growth Factor-β: Implications for Homeostasis," *Progress in Growth Factor Research 5*:341-351, Pergamon Press (1994).

Wahl, S.M., "Transforming Growth Factor β: The Good, the Bad, and the Ugly," *J. Exp. Med. 180*:1587-1590, Rockefeller University Press (1994).

\* cited by examiner

METHOD OF ADMINISTERING ANTIBIOTIC THERAPY FOR TREATING INTRACELLULAR INFECTIOUS DISEASES

TECHNICAL FIELD

The present invention is related to the use of immunomodulators to assist in the treatment of infectious diseases, specifically those caused by facultative intracellular microorganisms such as tuberculosis, leishmaniasis, trypanosomiasis, among others, that represent a great public health problem.

BACKGROUND OF THE INVENTION

Infectious diseases in developing countries continue to be one of the main causes of death, exceeding deaths from cardiovascular diseases and cancer. Infectious diseases include those provoked by facultative intracellular microorganisms, as is the case of tuberculosis (TB), which is the main cause of death among these diseases. The appearance of multi-resistant strains and the Acquired Immune Deficiency Syndrome (AIDS) have increased the incidence of this disease (Kochi A. The global tuberculosis situation and the new control strategy of the World Health Organization. Tubercle 1991, 72:1-6).

TB can also affect animals, principally domestic and farm animals such as cows, cats, dogs and fowl. Although other diseases, such as trypanosomiasis and leishmaniasis, represent a public health problem, their incidence is not as important as that of TB, but in all these diseases treatment is complicated due to the immunological changes patients present.

The AIDS pandemic has caused cases of pulmonary and extra-pulmonary tuberculosis to increase over the last decade, placing it as a priority disease for health programs in almost the whole world (Kochi A. The global tuberculosis situation and the new control strategy of the World Health Organization. Tubercle 1991, 72:1-6. Sudre P, ten Dam G, and Kochi A. Tuberculosis: a global overview of the situation today. Bull World Health Organ 1992; 70:149).

A person infected with the human immunodeficiency virus (HIV) has 10 times the risk of developing tuberculosis. In an HIV infected individual, the presence of other infections, including tuberculosis, can permit the virus to multiply more rapidly resulting in an accelerated progression of the infection. As the infection progresses, leukocytes decrease in number and function, the immune system is no longer able to prevent the growth and dissemination of *Mycobacterium tuberculosis*.

It is calculated that one third of the world population is infected with *Mycobacterium tuberculosis*. After infection, the risk of developing the disease is approximately 10%, and the remaining 90% continue with latent infection from the viable bacillus. This 10% amounts to 8 million persons reported each year with active tuberculosis, resulting in 3 million deaths a year (Kochi A. The global tuberculosis situation and the new control strategy of the World Health Organization. Tubercle 1991, 72:1-6. Sudre P, ten Dam G, and Kochi A. Tuberculosis: a global overview of the situation today. Bull World Health Organ 1992; 70:149). This disease is, moreover, a serious problem faced by patients undergoing hemodialysis.

Tuberculosis treatment is long term, and hence dropping-out is frequent. This has led to a reactivation of the disease and the appearance of strains that are multi-resistant to the medicines normally used. (isoniazid, ethambutol, pyrazinamide, rifampicin and a derivative of the latter, rifapentin) Transforming Growth Factor-beta Type (TGF-β)

TGF-β is the prototype of a superfamily of autocrine and paracrine factors that participate in the control of embryonic development, cell differentiation and proliferation, tissue repair and regulation of the immune system. TGF-β is a potent inhibitor of cell proliferation in lymphoid and epithelial lineages and failure in this antiproliferative response has been associated with the formation of malignant tumors, supporting the idea that TGF-β and its signal transducing molecules are authentic "tumor suppressors. TGF-β plays an important role in tissue repair.

Platelets release TGF-β in the site of a lesion, setting off a cascade of events leading to repair of the wound, a process in which TGF-β plays a preponderant role (Massagué, J. (1990). The transforming growth factor-β family. Annu Rev Cell Biol 6, 597-641. Massagué, J., Blain, S. W., and Lo, R. S. (2000). TGF-β signaling in growth control, cancer, and heritable disorders. Cell 103, 295-309)

Among the interleukins, TGF-β is a unique cytokine because it efficiently suppresses cell immunity by acting at several levels (Letterio J J, Roberts A B. Regulation of immune response by TGF-β. Annu Rev Immunol 1998; 16:137-61). As happens with many other types of cells, TGF-β inhibits the proliferation of lymphocytes, above all mature T cells that have already been activated (Kehrl J H, Wakefield L M, Roberts A B, Jakowlew S, Alvarez-Mon M, Derynck R, Sporn M, Fauci A S. Production of transforming growth factor beta by human T lymphocytes and its potential role in the regulation of T cell growth. J Exp Med 1986; 163: 1037-50), while virgin or inactivated T lymphocytes are relatively resistant to the antimitogenic effect of TGF-β. TGF-β also inhibits the proliferation of B lymphocytes and induces their cell death by apoptosis (Lomo J, Blomhof H K, Beiske K, Stokke T, Smeland E B. TGF-β1 and cyclic AMP promotes apoptosis in resting human B lymphocytes. J Immunol 1995; 154:1634-43) and suppresses the cytolytic differentiation and activity of NK and T cells (Letterio J J, Roberts A B. Regulation of immune response by TGF-β. Annu Rev Immunol 1998; 16:137-61). Another important inhibitory effect of TGF-β is suppression of the expression of the major histocompatibility complex (MHC) class 2 molecules in macrophages (Czarniecki C W, Chiu H H, Wong G H, Mc Cabe S M, Palladino M A. Transforming growth factor beta 1 modulates the expression of class II histocompatibility antigens on human cells. J Immunol 1988; 140:4217-4232), thus interfering in the antigen presentation process, avoiding T lymphocyte activation. The most important result of this interference in T cell activation is the inhibition of the secretion of interleukin 2 (IL-2), because this cytokine is an essentially inducing factor of cell proliferation. Indeed, it is considered that this is the principal mechanism through which TGF-β inhibits lymphocyte proliferation. Another T lymphocyte mitogenic cytokine and macrophage activator is interleukin 1 (IL-1).

TGF-β also directly and indirectly inhibits its production by suppressing its receptor specific expression and, at the same time, increasing the release of the IL-1 soluble receptor antagonist whose function is to trap and avoid the binding of this cytokine to its receptor (Turner M, Chantry D, Katsikis T, Berger A, Brennan F M, Feldman M. Induction of interleukin 1 receptor antagonist protein by transforming growth factor beta. J Immunol 1991; 21:1635-1639)

One of the fundamental suppressor effects of TGF-β on the immune system is the deactivation of macrophages, which can be carried out through direct inhibition of the production of oxygen free radicals and nitric oxide or, indirectly, by suppressing the production of macrophage activating cytokines such as the tumor necrosis factor alpha (TNF-α) and interferon gamma (INF-γ) and their receptors (Ranges G E, Figari I S, Espevik T, Palladino M A. Inhibition of cytotoxic T cell development by transforming growth factor beta and reversal by recombinant tumor necrosis factor alpha. J Exp Med 1987; 166:991-999. Pinson D M, Le Claire R D, Lorsbach R B, Parmely M J, Russell R. Regulation by transforming growth factor beta-1 of expression and function of the receptor for INF gamma on mouse macrophages. J Immunol 1992; 149:2028-2038). For the production of nitric oxide, it is necessary for TNF-α and INF-γ to activate the inducible nitric oxide synthetase enzyme (iNOS), and TGF-β inhibits both the transcription and translation of the gene encoding this enzyme (Vodovotz Y, Bogdan C. Control of nitric oxide synthase expression by transforming growth factor beta: implications for homeostasis. Prog Growth Factor Res 1994; 5:341-351). Furthermore, the participation of INF-γ is fundamental for the activation of macrophages as part of the Th-1 response, and one of the most efficient immunosuppressor effects of TGF-β is to inhibit the production of INF-γ and its receptor expressed on the macrophage membrane (Pinson D M, Le Claire R D, Lorsbach R B, Parmely M J, Russell R. Regulation by transforming growth factor beta-1 of expression and function of the receptor for INF gamma on mouse macrophages. J Immunol 1992; 149:2028-2038). TGF-β is an efficient promoter of Th-2 cytokines, particularly interleukin 10 (Schmitt E, Hoehn P, Huels C, Goedert S, Palm N, Rude E, Germann T. T helper type 1 development of naive CD-4 T cells requires the coordinated action of interleukin 12 and interferon gamma and is inhibited by transforming growth factor beta. Eur J Immunol 1994; 24:793-798. Strober W, Kelsall B, Fuss I, Marth T, Ludviksson B, Ehrhardt R, Neurath M. Reciprocal IFN gamma and TGF-β responses regulate the occurrence of mucosal inflammation. Immunol Today 1997; 18:61-64. Maeda Y, Kuwahara H, Ichimura Y, Ohtsuki M, Kurakata S, Shirahishi A. TGF-β enhances macrophage ability to produce IL-10 in normal and tumor bearing mice. J Immunol 1995; 15:49264932).

Sustained, excessive production of TGF-β has been implicated as an important pathogenic factor in the fibrosis and tissue damage present in different diseases (Wahl S M. Transforming growth factor beta: the good, the bad and the ugly. J Exp Med 1994; 180:1587-90). But apart from this important fibrosis inducing effect, in several chronic inflammatory diseases, such as rheumatoid arthritis, leprosy and tuberculosis, there is an anergy of cell immunity which as been attributed in part to excessive production of TGF-β (Letterio J J, Roberts A B. Regulation of immune response by TGF-β. Annu Rev Immunol 1998; 16:137-61. Wahl S M. Transforming growth factor beta: the good, the bad and the ugly. J Exp Med 1994; 180:1587-90. Tossi Z, Ellner J. The role of TGF-β in the pathogenesis of human tuberculosis. Clin Immunol Immunopathol 1998; 87:107-114). This pathogenic proposition has been strengthened by observations made in transgenic animals with overexpression of the TGF-β gene that suffer intense immunosuppression and also by the extensive multifocal inflammation presented by mice with disruption of the gene coding for TGF-β1 (Shull M M, Ormsby I, Kier A B, Pawloski S, Diebold R, Yin M, Allen R, Sidman C, Proetzel G, Calvin D. Targeted disruption of the mouse transforming growth factor beta 1 gene results in multifocal inflammatory disease. Nature 1992; 359:693-99). In animal models of infections from facultative intracellular germs such as leishmaniasis and trypanosomiasis, it has been observed that TGF-β is produced in excess favoring progression of the disease (Barral Netto M, Barral A, Brownell C E, Skeiki Y A, Ellingsworth L R, Twardzic D R, Reed S G. Transforming growth factor beta in leshmanial infection; a parasite escape mechanism. Science 1992; 257:545-48. Gazzinelli R T, Oswald I P, Hieny S, James S L, Sher A. The microbicidal activity of interferon gamma treated macrophages against *Trypanosoma cruzi*, involves an L-arginine-dependent, nitrogen oxide-mediated mechanism inhibitable by interleukin 10 and transforming growth factor beta. Eur J Immunol 1992; 22:2501-06). In human leishmaniasis and filariasis, the participation of TGF-β has also been documented in immunosuppression induction (Barral Neto M, Barral A, Brodskyn C Carvalho E M. Cytotoxicity in human mucosal and cutaneous leshmaniasis. Parasite Immunol 1995, 17:21-28. King C L, Mahanty S, Kumarasawami V, Abrams J S, Regunthan J, Jeyamaran K, Ottesen E A, Nutman T B. Cytokine control of parasite specific anergy in human lymphatic filariasis. J Clin Invest 1993, 92:1667-1673). In relation to viral infections, it has been observed that progressive immunodeficiency during AIDS is associated with a gradual increase of TGF-β (Lotz M, Seth P. TGF beta and HIV. Annu NY Acad Sci 1993, 685:501-511), and in cases of HIV and *M. tuberculosis* co-infection there is a synergistic potentiating effect on the production of TGF-β which increases viral activity accelerating the disease (Maltman J, Pargnell I B, Graham G J. Specificity and reciprocity in the interactions between TGF-β, and macrophage inflammatory protein 1-alpha. J Immunol 1996, 156:1566-1571).

*Mycobacterium tuberculosis*, its purified protein derivatives (PPD) and some of their molecular components, such as lipoarabinomannan, induce the macrophages to produce and secrete large amounts of TGF-β (Tossi Z, Ellner J. The role of TGF-β in the pathogenesis of human tuberculosis. Clin Immunol Immunopathol 1998; 87:107-114). The participation of INF-γ is fundamental in the activation of macrophages as part of the Th-1 response which is essential in the control of infectious diseases produced by facultative intracellular germs such as tuberculosis and leshmaniasis (Hernández Pando R, Orozco E H, Arriaga K, Sampieri A, Larriva Sahd J, Madrid M V. Analysis of the local kinetics and localization of interlukin 1 alpha, tumor necrosis factor alpha and transforming growth factor beta during the course of experimental pulmonary tuberculosis. Immunology 1997; 90:607-17). Due to the fact that TGF-β is an efficient blocker of INF-γ production and, at the same time, induces cytokine Th-2 production (Schmitt E, Hoehn P, Huels C, Goedert S, Palm N, Rude E, Germann T. T helper type 1 development of naive CD-4 T cells requires the coordinated action of interleukin 12 and interferon gamma and is inhibited by transforming growth factor beta. Eur J Immunol 1994; 24:793-798. Strober W, Kelsall B, Fuss I, Marth T, Ludviksson B, Ehrhardt R, Neurath M. Reciprocal IFN gamma and TGF-β responses regulate the occurrence of mucosal inflammation. Immunol Today 1997; 18:61-64. Maeda Y, Kuwahara H, Ichimura Y, Ohtsuki M, Kurakata S, Shirahishi A. TGF-β enhances macrophage ability to produce IL-10 in normal and tumor bearing mice. J Immunol 1995; 15:4926-4932), it contributes to the progression of these diseases. In experimental models of pulmonary tuberculosis and in the active human disease, a high production of TGF-β has been shown (Hernández Pando R, Orozco E H, Arriaga K, Sampieri A, Larriva Sahd J, Madrid M V. Analysis of the local kinetics and localization of interlukin 1 alpha, tumor necrosis factor alpha and transforming growth factor beta during the course of experimental pulmonary tuberculosis. Immunology 1997; 90:607-17. Hirsch C, Ellner J, Blinkhorn R, Tossi Z. In vitro restoration of T cell responses in tuberculosis and augmentation of monocyte effector function against *Mycobacterium tuberculosis* by natural inhibitors of transforming growth factor beta. Proc Natl Acad Scie 1997; 94:3926-3931), which coincides with the decrease in protective immunological activity mediated by the cytokines produced by lymphocytes Th-1 (INF-γ, IL-2) and TNF-α. In vitro studies have shown that the anergy of cell immunity that generally exists in patients with active pulmonary tuberculosis can be corrected with the administration of TGF-β blocker antibodies or natural blockers, which significantly reduces intracellular growth of the tuberculosis bacillus (Hirsch C, Ellner J, Blinkhorn R, Tossi Z. In vitro restoration of T cell responses in tuberculosis and augmentation of monocyte effector function against *Mycobacterium tuberculosis* by natural inhibitors of transforming growth factor beta. Proc Natl Acad Scie 1997; 94:3926-3931). Indeed, TGF-β neutralizing antibodies or decorin as a TGF-β inhibitor have been used in in vitro studies to promote the efficiency of the immune system in eliminating *M. tuberculosis*. (Hirsch C, Ellner J, Blinkhorn R, Tossi Z. In vitro restoration of T cell responses in tuberculosis and augmentation of monocyte effector function against *Mycobacterium tuberculosis* by natural inhibitors of transforming growth factor beta. Proc Natl Acad Scie 1997; 94:3926-3931) However, these products have the disadvantage of evoking the formation of antibodies that block their activity or decrease the efficiency of the anti-inflammatory activity of TGF-β, discouraging the use of these inhibitors.

The TGF-β signaling pathway begins on the cell surface with the association, mediated by this ligand, of type I and II receptors, which can be considered heteromeric sub-units of the "signaling receptor". Type I and II receptors are transmembrane proteins whose intracellular portions consist of serine and threonine protein kinases. The phosphorylation of the kinase of receptor I by the kinase of receptor II causes its activation and hence the phosphorylation of members of a novel family of proteins called "Smads", which form heteromeric complexes that migrate to the nucleus to regulate the transcriptional events involved in TGF-β responses (Massagué, J. (1998). TGF-β signal transduction. Annu Rev Biochem 67, 753-791. Massagué, J., and Chen, Y.-G. (2000). Controlling TGF-β signaling. Genes and Development 14, 627-644). As well as the signaling receptor, other cell surface proteins have been identified that bind TGF-β. Betaglycan and endoglin are transmembranal proteins with large extracellular domains capable of binding to TGF-β and small intracellular regions, very similar the one to the other. Betaglycan is present in most tissues and cell lines, except in the endothelium, in contrast, endoglin is principally expressed in the latter. Although none of these glycoproteins seem to have a clear function in the TGF-β intracellular transduction pathway, both seem to modulate the extracellular access of the ligand to type I and II receptors (Massagué, J., and Chen, Y.-G. (2000). Controlling TGF-β signalling. Genes and Development 14, 627-644).

Betaglycan, also known as TGFβ, type III receptor is a transmembranal proteoglycan containing glycosaminoglycans (GAG) of the heparan and chondroilin sulfate type that belongs to a new class of receptors called "co-receptors", because of their capacity to modulate ligand interaction with the signaling receptors. Even devoid of GAG, betaglycan binds the three different TGF-β isoforms with high affinity. Due to this high affinity, the presence of betaglycan compensates for the low affinity these signaling receptors have for the ligand, thus permitting equipotentiation of the different TGF-β isoforms. This effect seems to be mediated by the capacity of betaglycan to associate with TGFβ and receptor II in a tripartite complex of "ligand presentation" (Esparza-López, J., Montiel, J. L., Vilchis-Landeros, M. M., Okadome, T., Miyazono, K., and López-Casillas, F. (2001). Ligand binding and functional properties of betaglycan, a co-receptor of transforming growth factor-β superfamily. Specialized binding regions for transforming growth factor-β and inhibin A. J Biol Chem 276, 14588-14596). Although the capacity to equipotentiate the TGF-β isoforms is one of the best characterized functions of betaglycan, Barnett et al. demonstrated that the presence of betaglycan is indispensable for the adequate formation of the embryonic primordia that give origin to the cardiac valves (a process that depends on the presence of TGF-β), which leads to the belief that some of the regulating effects of TGF-β on the embryonic development depend on the direct participation of this co-receptor in signaling mechanisms (Brown, C. B., Boyer, A. S., Runyan, R. B., and Barnett, J. V. (1999). Requirement of type III TGF-β receptor for endocardial cell transformation in the heart. Science 283, 2080-2082). As well as the membranal form of betaglycan, there is a "soluble" form which is found in serum and extracellular matrixes. This has its origin in a juxtamembrane proteolytic escision that releases the receptor ectodomain from its anchorage to the membrane. The recombinant form of soluble betaglycan has been shown to have a opposite function to the membranal form, that is a potent neutralizing agent of the effects of TGF-β (López-Casillas, F., Payne, H. M., Andres, J. L., and Massagué, J. (1994). Betaglycan can act as dual modulator of TGF-β access to signaling receptors: mapping of ligand binding and GAG attachment sites. J Cell Biol 124, 557-568. Vilchis-Landeros, M. M., Montiel, J. L., Mendoza, V., Mendoza-Hernández, G., and López-Casillas, F. (2001). Recombinant soluble betaglycan is a potent and isoform-selective transforming growth factor-β neutralizing agent. Biochemical Journal 355, 215-222). These studies conducted in vitro with tissue cells in culture have made it possible to define betaglycan as an "extracellular switch" that modulates the effects of TGF-β (Attisano, L., Wrana, J. L., López-Casillas, F., and Massagué, J. (1994). TGF-β receptors and actions. Biochim Biophys Acta 1222, 71-80).

Prostaglandins

Prostaglandins are potent mediators of intercellular communication, and prostaglandin E2 (PGE2) in high concentrations acts as an immunosuppressor mechanism for immunity mediated by T cells (Phipps R P, Stein S H, Roper R L. A new view of prostaglandin E regulation of the immune response. Immunol Today 1991; 12:349-52). Certain cell signals are accompanied by a rapid rearrangement of the cell membrane lipids through the activation of lipases that generate bioactive lipids that can serve as intra and/or extracellular mediators. The most important of these lipids is arachidonic acid, a poly-unsaturated fatty acid of 20 carbons, that is normally esterified in phospholipids of the cell membrane and is released through the activation of cell phospholipases (Serhan C N, Haeggström J Z, Leslie C C. Lipid mediator networks in cell signaling: update and impact of cytokines. FASEB J 1996; 10:1147-58). The products derived from the metabolism of arachidonic acid are the so-called eicosanoides, which are considered to be autacoids because they are short scope local hormones that are rapidly formed and have a local effect and their activity falling spontaneously or by the effect of enzyme degradation. Eicosanoids affect many physiological and pathological events, they are synthesized by two major classes of enzymes: cyclooxygenases (COX) and lipoxygenases which produce, prostaglandins and leukotrienes, respectively (Phipps R P, Stein S H, Roper R L. A new view of prostaglandin E regulation of the immune response. Immunol Today 1991; 12: 349-52. Serhan C N, Haeggström J Z, Leslie C C. Lipid mediator networks in cell signaling: update and impact of cytokines. FASEB J 1996; 10:1147-58). The cyclooxygenase pathway is mediated by two different enzymes: COX-1, which is a constitutively expressed enzyme, and COX-2, which is a highly inducible enzyme expressed in the inflamed tissue after exposure to growth factors, cytokines and other inflammation mediators. Of the prostaglandins, the most extensively studied are those of series E (PGE). There is evidence showing that PGE-2 has an important immunosuppressor effect, including a decrease in lymphocyte proliferation, NK activation and MHC-II expression (Goto T R, Herberman R B, Maluish A, Strong D M. Cyclic AMP as a mediator of prostaglandin E induced suppression of human natural killer cell activity. J Immunol 1983; 130:1350-55. Snyder D S, Beller D I, Unanue E R. Prostaglandins modulate macrophage expression. Nature 1982; 299:163-65). It has also been found that PGE-2 play a predominant role in the regulation of the Th1 and Th2 type response. Indeed, PGE-2 inhibits the production of Th1 cytokines, interferon gamma, interleukin 2 and 12, blocks the activation of macrophages and suppresses the production of interleukin 1 and TNF-α (Betz M, Fox B S. Prostaglandin E2 inhibits production of Th-1 lymphokines but not of Th-2 lymphokines. J Immunol 1991; 146:108-13. Kuroda E, Suguira T, Zeki K, Yoshida Y, Yamashita U. Sensitivity difference to the suppressive effect of prostaglandin E2 among mouse strains: a possible mechanism to polarize Th2 type response in BALB/c mice. J Immunol 2000; 164: 2386-95). This activity of PGE-2 may be important in intracellular infections, since it has been shown in mice and humans that infection from mycobacteria is controlled by the activation of macrophages through the production of Th1 cytokines (Rook G A W, Hernández Pando R. Pathogenesis of tuberculosis. Annual Rev Microbiol 1996, 50:259-284).

Tuberculosis is a disease that is treated with antibiotics that need to be administered for 6 months in combination with 3 different antibiotics and this causes a high treatment drop-out frequency by patients generating frequent relapses and resistance to the antibiotics (Rook G A W, Hernández Pando R. Pathogenesis of tuberculosis. Annual Rev Microbiol 1996, 50:259-284). Thus, one alternative would be to design new treatment schemes making it possible to shorten the antibiotic therapy. Another excellent example of this situation occurs with leprosy.

One potentially useful therapeutic strategy in diseases with this immunological pattern is immunotherapy, that consists in administering substances that favor the protective immune response. Considering the prominent immuno-regulator role played by TGF-β and prostaglandins during infection by facultative intracellular microorganisms, we have developed the present invention with the purpose of assisting the treatment by developing the response of the organism to defend itself against facultative intracellular microorganisms, especially against the genus *Mycobacterium, Leishmania, Trypanosoma* among others, in an attempt to inhibit the immunosuppressor effect of TGF-β but, in turn, mitigating in another way, the pro-inflammatory side effect resulting from its inhibition.

For this reason, we have developed the present invention with the purpose of assisting the treatment of diseases caused by facultative intracellular organisms in order to reduce antibiotic treatment time and, in a secondary way, by shortening the application time for these treatments, decrease the drop-out percentage.

DETAILED DESCRIPTION OF THE INVENTION

With clear knowledge of the immune response in infections by facultative intracellular microorganisms, the present invention was developed by integrating a treatment kit as complement to the antibiotic therapy used in these infections. The treatment kit is based on the selective inhibition of the undesirable effects caused by TGF-β in the immune response installed in these infections leading to the cell immunity suppression that is present in advanced stages of these diseases, specifically in TB. The treatment kit preferably uses a soluble betaglycan that is a natural antagonist of TGF-β instead of using neutralizing antibodies or decorin, since soluble betaglycan fulfils the same purpose but more effectively, for in principle it has advantages over the neutralizing antibodies because it is a "natural antagonist", hence its administration should not evoke the formation of antibodies that can block its activity.

With clear knowledge of the functions of TGF-β, we determined two possible effects that would arise by blocking its activity. One of them can be considered to be beneficial since, without its action, cell immunity is reactivated. In the other, however, we found a considerable increase in inflammation in our experimental models that caused tissue damage, because TGF-β is a powerful anti-inflammatory cytokine. From these preliminary studies, it was possible to determine that treatment could not be exclusively with a selective TGF-β blocker, but that it would also be extremely important to mitigate the pro-inflammatory side effect resulting from inhibiting TGF-β.

Having extensively studied the cell response process in infections by facultative intracellular microorganisms in which, in the progressive phase of the inflammation caused by the disease, there is excessive production of prostaglandins, principally of type E. Hence, the following step in the development of this kit, was to include a prostaglandin inhibitor.

To said effect, an experimental model was used in mice that were administered with the treatment kit consisting of a natural selective TGF-β inhibitor. We specifically used soluble betaglycan associated with a generic prostaglandin inhibitor, and we specifically used indometacine, which is well known for its effect in inhibiting COX 1 and 2. However, on using a generic prostaglandin inhibitor, undesirable side effects presented because, although the beneficial effect expected was produced, the protective effect of the constitutive prostaglandin particularly on the gastric mucosa was also blocked, producing extensive erosive gastritis that caused greater damage than the TB itself.

From these observations in our experimental models, we determined the most adequate way of integrating the treatment kit to assist in the antibiotic therapy of diseases caused by facultative intracellular microorganisms, firstly, with a selective TGF-β inhibitor associated with a selective induced PGE inhibitor. This is achieved using a drug that can block COX 2 in a highly specific manner, thus inhibiting the excessive inflammatory effect produced by blocking the action of TGF-β with the soluble betaglycan and with no effect on the gastric mucosa.

The pharmaceutical products that are known to selectively inhibit COX-2 include niflumic acid, nimesulide and mefamic acid. In order to prove the protective effect of the treatment kit, we carried out different experiments to evaluate the performance of these three products, finding that niflumic acid presented the best result by inhibiting 98% of the formation of PGE, while the other two, blocked 80 to 85% of PGE formation.

Examples of Use

In order to evaluate the effectiveness of the immunotherapeutic effect of soluble betaglycan, we chose tuberculosis, one of the diseases caused by facultative intracellular microorganisms, without this limiting the scope of the use of the present invention, and it is referred to here as one of the examples of use. In order to be in a condition to demonstate the effectiveness of the treatment, we developed an experimental model of pulmonary tuberculosis in BALB/c mice through the intra-tracheal injection of one million live, virulent tuberculosis bacilli. The experimental model (Hernández Pando R, Orozco E H, Arriaga K, Sampieri A, Larriva Sahd J, Madrid M V. Analysis of the local kinetics and localization of interlukin 1 alpha, tumor necrosis factor alpha and transforming growth factor beta during the course of experimental pulmonary tuberculosis. Immunology 1997; 90: 607-17. Hernández Pando R, Orozco E H, Sampieri A, Pavón L, Velaswuillo C, Larriva S J, Madrid M V. Correlation between the kinetics of Th1/Th2 cells and pathology in a murine model of experimental pulmonary pathology. Immunology 1996; 89:26-33) uses male BALB/c mice, 6 to 8 weeks old. A reference strain of *Mycobacterium tuberculosis* was used that was cultured in specific commercial media. After the time required for their growth, the bacilli were harvested and kept frozen until they were used. Before using them, the amount and viability of the bacilli was checked. Pulmonary tuberculosis was induced in the mice through an incision along the medial line of the trachea, having previously anesthetized the mice, and they were injected with a sufficient amount of viable bacteria in suspension to generate the infection. The incision was sutured and the animals kept in conditions of isolation.

This model allowed us to confirm that the activated TNF-$\alpha$ produced by macrophages and type 1 helper T lymphocytes (Th1) that produce IFN-$\gamma$ and IL-2 are responsible for protecting against the tuberculosis bacillus, while the type 2 helper T cells antagonize the Th-1 response and divert the cell immune response to humoral immunity with which the progression of the disease is facilitated (Rook G A W, Hernández Pando R. Pathogenesis of tuberculosis. Annual Rev Microbiol 1996, 50:259-284. Seah Gt, Scott M, Rook G A W. Type 2-cytokine-gene activation and its relationship to extent of disease in patients with tuberculosis: J Infect Dis 2000; 181: 385-389). In this model, during the first month of infection, there is clear predominance of the Th-1 protective response with which the infection is controlled. Subsequently, there is a progressive increase in Th-2 activity which decreases the efficiency of the immunological protection, permitting the disease to progress as there is a greater number of bacteria with extensive pulmonary lesions (pneumonia) which lead to death. During the advanced phase of the infection, there is a high level of production of TGF-$\beta$, which is a factor that deactivates macrophage function and stimulates Th-2 cell activity (Hernández Pando R, Orozco E H, Arriaga K, Sampieri A, Larriva Sahd J, Madrid M V. Analysis of the local kinetics and localization of interlukin 1 alpha, tumor necrosis factor alpha and transforming growth factor beta during the course of experimental pulmonary tuberculosis. Immunology 1997; 90:607-17). The intraperitoneal administration of the soluble form of betaglycan during the advanced phase of the disease blocks TGF-$\beta$ activity, which reactivates the Th-1 response producing a significant decrease in the bacillary load. However, because TGF-$\beta$ is an efficient anti-inflammatory factor, the extent of the pneumonia increased in the mice treated with soluble betaglycan by blocking the effect of TGF-$\beta$. In order to avoid this problem, an anti-inflammatory drug was added to the treatment. Niflumic acid was chosen because it is a selective cyclooxygenase 2 blocking agent, blocking the synthesis of prostaglandins that are also produced in high concentrations during the advanced phase of the infection and that participate by stimulating Th-2 cells (Betz M, Fox B S. Prostaglandin E2 inhibits production of Th-1 lymphokines but not of Th-2 lymphokines. J Immunol 1991; 146:108-13. Kuroda E, Suguira T, Zeki K, Yoshida Y, Yamashita U. Sensitivity difference to the suppressive effect of prostaglandin E2 among mouse strains: a possible mechanism to polarize Th2 type response in BALB/c mice. J Immunol 2000; 164:2386-95). The joint administration of soluble betaglycan with niflumic acid produced greater stimulation of the protective immune response which further decreased the amount of tuberculosis bacilli in the lung than in comparison with soluble betaglycan alone.

In order to determine the optimum dose of soluble betaglycan that blocks TGF-$\beta$ activity, in this experimental model we carried out dose-response experiments in chronically infected mice, determining the colony forming units in the lungs and the cutaneous delayed-type hypersensitivity (DTH) response as evaluation parameters. Subsequently, we carried out experiments with two treatment schemes, the first with soluble betaglycan alone which was started on day 30 post-infection, on which the late phase of the disease begins and TGF-$\beta$ reaches and maintains high concentrations. Another group additionally received an efficient anti-inflammatory to avoid damage from the excessive inflammation generated on suppressing the effect of TGF-$\beta$. Niflumic acid, a drug that specifically blocks cyclooxygenase 2 (COX-2), thus limiting prostaglandin synthesis, was chosen.

The control group with no treatment whatever showed a progressive increase in pneumonia, beginning on day 28 of the infection and affecting more than 60% of the lung surface by day 60. The groups that only received soluble betaglycan presented 30% more pneumonia than the control group after two months of treatment. The group to which specific antibodies to TGF-$\beta$ was administered also presented an increase in pneumonia, confirming that this side effect was due to the blocking of TGF-$\beta$. Treatment with niflumic acid alone, or in combination with soluble betaglycan or anti-TGF-$\beta$ antibodies, decreased the area affected by pneumonia by 25% in relation to the control group after two months of treatment. The bacteria colony forming units (CFU) progressively increased in the control group without treatment, while they decreased significantly after 30 days of treatment with soluble betaglycan anti-TGF-$\beta$ antibodies and niflumic acid. After 60 days of treatment, the animals treated with anti-TGF-$\beta$ antibodies showed the same levels of colony forming units as the control group, while those treated with soluble betaglycan showed 50% less CFU. The animals treated with the combination of soluble betaglycan and niflumic acid showed the most notable decrease in CFU, 20 times less than in the control group.

The suppression of TGF-$\beta$ activity during the late phase of the infection induced an increase in the expression of IL-2, TNF-$\alpha$, IFN-$\gamma$ and nitric acid synthetase, while interleukin 10 expression decreased. The animals treated with niflumic acid also showed the same pattern, but the combination of soluble betaglycan and niflumic acid after 60 days of treatment produced the highest expression of Th-1 cytokines.

The DTH response of the control group decreased progressively, while the response in all the treated mice was greater, particularly in those treated with niflumic acid and betaglycan. With this treatment kit, we were able to enhance the immune response of the treated animals and the treatment period with conventional antibiotics was shortened.

The preferred way of carrying out the invention, is the preparation of a kit that contains a selective TGF-$\beta$ inhibitor, preferably soluble betaglycan associated with a selective induced PGE inhibitor, preferably niflumic acid to be administered jointly with the usual treatment with antibiotics in diseases caused by facultative intracellular microorganisms, such as tuberculosis, trypanosomiasis, leishmaniasis, leprosy, among others. In general terms, we saw better results, without this being a limiting factor, when starting with the selective induced PGE inhibitor, preferably niflumic acid in daily doses that are therapeutically effective in producing its inhibition effect, associated with the natural selective TGF-β inhibitor administered in therapeutically effective doses, preferably soluble betaglycan twice a week parenterally in doses of 0.5 to 2 mg per Kg of weight, administered concomitantly with the antibiotic therapy. Indeed, it is perfectly feasible to design ways and routes for administering the treatment kit that are different to those presented in this example of use, for example soluble betaglycan can be used in its wild, recombinant and/or mutant form, providing it conserves the TGF-β neutralization capacity, in parenteral administration forms; the pharmaceutically acceptable vehicle can be an isotonic saline solution, DNA vectors for heterologue expression such as the adenovirus in viral gene-therapy, DNA transfer or even a preparation for the administration of soluble betaglycan and its derivatives using an aerosol as administration vehicle via the respiratory route.

In general terms, the kit is designed so that soluble betaglycan can be administered in different forms and administration routes as mentioned in the paragraph above. The preferred form is twice a week, in doses ranging from 0.5 to 2 mg per Kg, together with niflumic acid supplied in daily doses, both in a pharmaceutically acceptable vehicle. This treatment kit is used to support the conventional treatment with antibiotics for infections by facultative intracellular microorganisms and in no way should it substitute it.

Another of the objectives of this treatment kit, is to shorten the therapy time for these diseases, thus permitting a decrease in the percentage drop-out from treatment over the prolonged periods of time required and, in turn, a decrease in multi-drug resistance for the same reason.

The invention claimed is:

1. A method to enhance an immune response in a mammal during the antibiotic treatment of an infection caused by *Mycobacterium tuberculosis*, comprising administering a soluble betaglycan and niflumic acid.

2. The method of claim 1, wherein the niflumic acid is administered daily.

3. The method of claim 1, wherein the soluble betaglycan is administered twice a week.

4. The method of claim 1, wherein the soluble betaglycan is administered at a dose of 0.5 to 3 mg per kilogram of body weight.

5. The method of claim 1, wherein the soluble betaglycan is administered at a dose of 0.5 to 2 mg per kilogram of body weight.

6. The method of claim 1, wherein the soluble betaglycan is administered in a pharmaceutical composition comprising a pharmaceutically acceptable vehicle, and the niflumic acid is administered in a pharmaceutical composition comprising a pharmaceutically acceptable vehicle.

7. The method of claim 1, wherein the soluble betaglycan and the niflumic acid are administered in a pharmaceutical composition comprising the soluble betaglycan, the niflumic acid, and a pharmaceutically acceptable vehicle.

8. The method of claim 1, wherein the length of the antibiotic treatment for treating the infection is shorter than the length of the antibiotic treatment for treating the infection without the administration of a soluble betaglycan and niflumic acid.

9. The method of claim 8, wherein the antibiotic treatment is during the late phase of infection.

* * * * *